United States Patent [19]

Idemoto et al.

[11] Patent Number: 4,832,683
[45] Date of Patent: May 23, 1989

[54] SURGICAL INSTRUMENT

[75] Inventors: Morito Idemoto; Yasuo Noguchi, both of Yokohama, Japan

[73] Assignee: Sumitomo Bakellite Company Limited, Tokyo, Japan

[21] Appl. No.: 60,394

[22] PCT Filed: Jul. 15, 1986

[86] PCT No.: PCT/JP86/00361
§ 371 Date: May 15, 1987
§ 102(e) Date: May 15, 1987

[87] PCT Pub. No.: WO87/01575
PCT Pub. Date: Mar. 26, 1987

[30] Foreign Application Priority Data

Sep. 20, 1985 [JP] Japan ................................ 60-206681

[51] Int. Cl.$^4$ .............................................. A61B 17/20
[52] U.S. Cl. ...................................... 604/22; 128/305; 433/86; 433/119
[58] Field of Search ............... 128/24 A, 305; 604/22, 604/27, 35, 19, 264, 272, 278; 433/86, 90, 118, 119

[56] References Cited

U.S. PATENT DOCUMENTS

| 2,270,607 | 1/1942 | Ryschkewlisch | 128/305 |
| 2,714,890 | 8/1955 | Vang . | |
| 2,845,072 | 7/1958 | Shafer . | |
| 2,874,470 | 2/1959 | Richards | 128/24 A |
| 2,984,241 | 5/1961 | Carlson | 433/118 |
| 3,368,280 | 2/1968 | Friedman et al. | 128/24 A |
| 3,433,226 | 3/1969 | Boyd . | |
| 3,526,219 | 9/1970 | Balamuth | 128/305 |
| 3,589,363 | 6/1971 | Banko et al. | 604/22 |
| 3,832,776 | 9/1974 | Sawyer . | |
| 3,862,630 | 1/1975 | Balamuth . | |
| 3,911,579 | 10/1975 | Lane et al. | 30/346.53 |
| 4,188,952 | 2/1980 | Loschilov et al. . | |
| 4,428,748 | 1/1984 | Peyman et al. | 604/22 |
| 4,526,571 | 7/1985 | Wuchinich | 604/22 |
| 4,531,934 | 7/1985 | Kossovsky et al. | 604/22 |
| 4,689,040 | 8/1987 | Thompson | 604/22 |

FOREIGN PATENT DOCUMENTS

A972146 1/1951 France .

OTHER PUBLICATIONS

Howmedica Inc.; Catalog (on or before 1985).

Primary Examiner—Stephen C. Pellegrino
Assistant Examiner—Mario Costantino
Attorney, Agent, or Firm—Browdy and Neimark

[57] ABSTRACT

A surgical instrument for cutting and separating biological tissue by employing ultrasonic vibration, particularly for cutting bones, separating the periosteum, and cutting and separating a coherent mass such as a calcium mass. An ultrasonic vibration-transmitting tool (5) which is connected to an ultrasonic vibration source (4) and performs mechanical vibration at the frequency of the ultrasonic waves has a spoon-shaped working portion (7) which is provided with at least one of a blade-shaped portion (25) forming a predetermined angle with respect to the direction of the mechanical vibration at the frequency of the ultrasonic waves and a blade-shaped portion (23, 24) substantially parallel with the direction of the vibration, the spoon-shaped working portion being adapted to be brought into contact with the biological tissue, and a liquid passage (21) passing through the interior of the ultrasonic vibration-transmitting tool, the liquid passage having an opening (22) which opens into the working portion. Further, by making of ceramic the whole part or the surface portion of the working portion (7) which is provided with the blade-shaped portion to be brought into contact with the biological tissue, it is possible to prevent wear deformation of the blade-shaped portion, and also to prevent transmission of electrical shocks to the nervous tissue in the event of a simple electrical fault state.

6 Claims, 2 Drawing Sheets (a)

(b)

SURGICAL INSTRUMENT

TECHNICAL FIELD

The present invention relates to a surgical instrument for cutting and separating biological tissue through ultrasonic vibration.

BACKGROUND ART

Conventionally, in bone-cutting operations and other like operations in neurosurgery and plastic surgery, such instruments or tools as Kerrison forceps, rongeur, drills, surgical knives, and gouges (round type only) have been used in order to cut and separate biological tissues, particularly hard bone tissue, cartilage tissue, and periosteum. However, there were disadvantages that the efficiency in tissue-cutting/separating work was low and long time was required, and heavy work load was imposed on the surgeon and a high level of technique was required.

Next, cutting tools, which use an electromotor or a pneumatic motor as a driving source, are used particularly for cutting hard bones. They make the rotational movement of the motor change to a linear movement by a cam or the like, and vibrate a cutting tool the tip of which is provided with saw teeth which are made of a metal. The amplitude of the vibraion of the cutting tool is on the order of 0.5 to 5 mm, while the frequency is on the order of 1 to 5 KHz. The cutting speed is affected by the magnitude of amplitude. However, since the cutting tool is vibrated at an amplitude on the order of 0.5 to 5 mm, if the cutting tool should be brought into contact with nervous tissue during cutting, there was a fear of injuring nervous tissue.

Further, a number of surgical instruments which employ ultrasonic waves have been developed. Surgical instruments have been known (for example, Japanese Patent Examined Publication No. 47-39197, and U.S. Pat. No. 3,589,363) in which the working portion connected to a source of ultrasonic vibration is ultrasonically vibrated, and soft tissues, other than elastic tissues such as blood vessels, with which the working portion is brought into contact, are crushed and removed by suction. A surgical instrument (for example, Japanese Patent Examined Publication No. 51-46,990, and U.S. Pat. No. 4,188,952) was developed for use in cutting and separating hard and soft tissues, and is connected to the source of ultrasonic vibration and provided with a metal working portion having saw-like cutting teeth. A surgical instrument (for example, U.S. Pat. Nos. 2,714,890, 2,845,072, and 3,832,776) is provided with a knife-shaped blade made of metal and a surgical instrument which has a bone marrow cavity rasp, for example, the SONIC SURGERY System which is a product of Howmedica Inc.

However, it is difficult to apply surgical instruments which crush and remove through suction biological tissues by utilizing ultrasonic vibration to cut biological tissues, particularly hard tissue such as bones. Further, although it is possible to apply a surgical instrument having a bone marrow rasp connected to a source of ultrasonic vibration to the cutting of soft bones and hard bones, it is difficult to apply it to the cutting and separating of periosteum, etc., since it may break biological tissue on the location of the cut surface due to the frictional heat of the rasp. In the case of a continuous operation, the surgical instrument is heated due to the ultrasonic vibrations and the mechanical strength of the surgical instrument per se is reduced. Furthermore, a surgical instrument which has a metal working portion connected to a source of ultrasonic vibration involves the fear that the cutting speed may be reduced during the process of repetitively cutting hard tissue such as bones because of deformation due to wear of the cutting teeth of the blade. In addition, since the working portion which is brought into contact with biological tissue is made of metal, there is a risk that a simple electrical fault could cause an electrical shock to the nervous tissue.

The present invention is aimed at providing, for solving such problems of the conventional surgical instruments, a surgical instrument for use in cutting and separating of biological tissue, particularly periosteum, etc., which allows the efficiency of the cutting and separating work by employing ultrasonic vibration to be improved, prevents biological tissue brought into contact with the working portion from being destroyed and broken due to frictional heat generated during the cutting and separating work, prevents mechanical strength of the working portion from being reduced due to heat generation during a continuous operation, or prevents the metal blade of the surgical instrument from being worn and deformed and prevent electrical shocks from being applied to nervous tissue in the event of a simple electric fault.

DISCLOSURE OF INVENTION

Namely, the present invention provides a surgical instrument for cutting and separating biological tissue by employing ultrasonic vibration, in which an ultrasonic vibration-transmitting tool, which is connected to a source of ultrasonic vibration and performs mechanical vibration at the frequency of the ultrasonic waves, includes a spoon-shaped working portion which is provided with at least one of a blade-shaped portion forming a predetermined angle with respect to the direction of mechanical vibration at the frequency of the ultrasonic waves and a blade-shaped portion substantially parallel with the direction of the mechanical vibration, the spoon-shaped working portion being adapted to be brought into contact with the biological tissue, and a liquid passage passing through the interior of the tool, the liquid passage having an opening which opens into the working portion.

Preferably, the whole part or the surface portion of the spoon-shaped working portion which is provided with a blade-shaped portion to be brought into contact with the biological tissue is made of a ceramic material.

BEST MODE FOR CARRYING OUT THE INVENTION

The present invention will be described below in detail with reference to the drawings.

Figure 1:
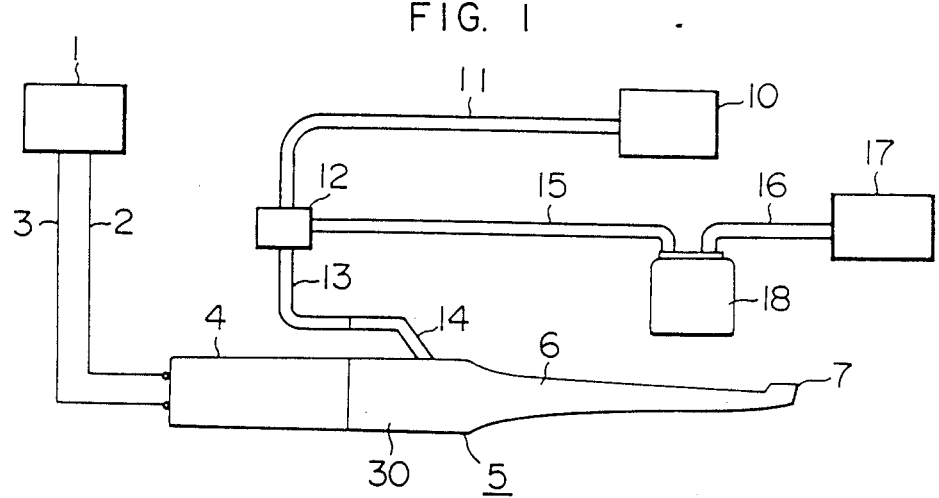
FIG. 1 is a view showing the relative arrangement between a surgical instrument in accordance with an embodiment of the present invention and an actuating device for actuating the same.
Figure 2:
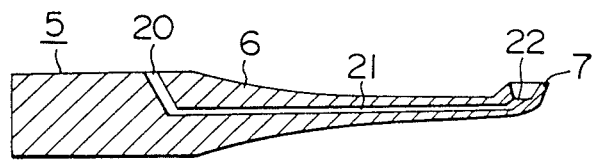
FIG. 2 is a schematic sectional view of an ultrasonic vibration-transmitting tool of the surgical instrument.

FIG. 1 is a view showing the relative arrangement between a surgical instrument in accordance with an embodiment of the invention and an actuating device for actuating the same. The surgical instrument as shown in the same figure is provided with an ultrasonic vibration source 4 and an ultrasonic vibration-transmitting tool 5 connected to thereto. The ultrasonic vibration-transmitting tool 5 has a base portion 30 which has a large diameter and is connected to the ultrasonic vibration source 4, a connecting portion 6 which extends from the base portion 30 in a substantially parallel direction with respect to the direction of mechanical vibration of the ultrasonic vibration source 4, and a spoon-shaped working portion 7 which is provided at the tip end of the connecting portion 6. The cross-sectional area of the connecting portion 6 is gradually decreased from the base portion 30 toward the working portion 7, so that the mechanical vibration at the frequency of the ultrasonic wave transmitted from the ultrasonic vibration source 4 to the ultrasonic vibration-transmitting tool 5 is enlarged at the connecting portion 6 and is transmitted to the working portion 7. As shown in FIG. 2, a liquid passage 21 is formed within the ultrasonic vibration-transmitting tool 5, which extends longitudinally of the tool 5. The passage 21 has at its left and right ends thereof an opening 20 connected to a pipe 14 and an opening 22 opened to the working portion 7, respectively.

When an ultrasonic wave-generating circuit 1 sends electric signals having the frequency of the ultrasonic waves to the ultrasonic vibration source 4 via cables 2 and 3, the ultrasonic vibration source 4 generates mechanical vibration having the frequency of the ultrasonic waves. Either the magnetostriction type or the electrostriction type may be used as the ultrasonic vibration source 4. The mechanical vibration having the frequency of the ultrasonic waves generated by the ultrasonic vibration source 4 is propagated to the ulrasonic vibration-transmitting tool 5, enlarged at the connecting portion 6 of the ultrasonic vibration-transmitting tool 5, and propagated to the working portion 7. The working portion 7 is brought into direct contact with biological tissue so that the biological tissue may be cut and separated by the mechanical vibration at the frequency of the ultrasonic waves. Further, the direction of the mechanical vibration at the frequency of the ultrasonic waves of the working portion 7 may be selected in accordance with the condition of the operation to be performed, for instance, the longitudinal direction with respect to the axis of the connecting portion 6 or the transverse direction with respect to the same, and is not specifically limited.

In the case where a liquid such as a solution liquid is to be supplied to the working portion 7 while the working portion 7 mechanically vibrates at the frequecy of the ultrasonic waves, the solution liquid is supplied from a liquid injecting device 10 to the same through a tube 11, a selector valve 12, a tube 13, and the pipe 14. Although the kind of solution is not specifically limited, solutions which have little effect on biological tissue, such as physiological saline, are preferable. As shown in FIG. 2, the solution which is led through the pipe 14 enters into the opening 20, through the liquid passage 21, and flows out from the opening 22 of the spoon-shaped working portion 7. By this liquid, the working portion 7 is kept cool, thus making it possible to prevent any rise in the temperature of the working portion 7 due to frictional heat generated in the process of cutting and separating work by the mechanical vibration at the frequency of the ultrasonic waves. Further, heat generation in the ultrasonic vibration-transmitting tool 5 during continuous use of the instrument is inhibited, thus making it possible to prevent reduction in the mechanical strength of the ultrasonic vibration-transmitting tool 5. Although the material of the ultrasonic vibration-transmitting tool 5 is not specifically limited, titanium alloys which have high tensile strength and fatigue endurance are preferable.

In the case where the removal through suction of fine places of the biological tissue which have been cut and separated by the mechanical vibration of the working portion 7 is to be performed, the tube 13 is connected to the tube 15 by the operation of the selector valve 12 after the cutting and separating operation, and the fine pieces of tissue together with the used solution are sucked by a suction device 17 from the opening 22 at the working portion 7 of FIG. 2 through the liquid passage 21, the opening 20, the pipe 14 in FIG. 1, the tube 13, the selector valve 12 and the tube 15 to be discharged into a bottle 18.

Figure 5:
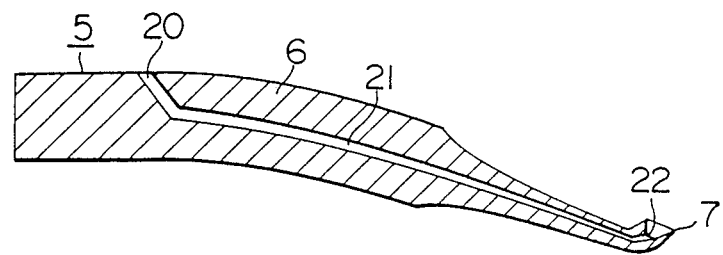
FIG. 5 is a view showing a modification of the ultrasonic vibration-transmitting tool in FIG. 2.

FIG. 5 shows a modification of the ultrasonic vibration-transmitting tool shown in FIGS. 1 and 2. Namely, in the ultrasonic vibration-transmitting tool 5 of FIG. 5, a connecting portion 6 of the ultrasonic vilbration-transmitting tool is inclined with respect to the direction of the mechanical vibration of the ultrasonic vibration source 4 at a predetermined angle and which extends in a curved manner. In this case, the direction of the mechanical vibration of the connecting portion 6 is the same direction as the axis of the connecting portion 6, i.e., the longitudinal direction of the connecting portion 6. The ultrasonic vibration-transmitting tool 5 shown in FIG. 5 has a length which is slightly longer in total than that of the ultrasonic vibration-transmitting tool 5 shown in FIGS. 1 and 2, and has a curved shape. By virtue of this, it can be suitably used in operations being undertaken in the most inaccessible or narrow locations, for instance, in cutting bones in the innermost part of the oral cavity. The total length and configuration of the ultrasonic vibration-transmitting tool 5, the angle at which the connecting portion 6 is disposed with respect to the direction of the mechanical vibration generated by the ultrasonic vibration source 4, or the like are not specifically limited, and may be selected in accordance with the position and configuration of the portion of the body to be operated on.

Figure 3:
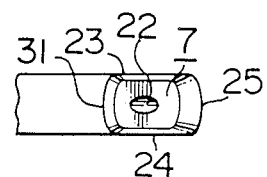
FIG. 3 is a view from above of a working portion of the ultrasonic vibration-transmitting tool in FIG. 2, drawn to an enlarged scale.

The working portion 7, as shown in FIG. 2, has a spoon-shaped configuration which opens upwardly. The peripheral ridge of the spoon shape forms blade-shaped portions. More specifically, as shown in FIG. 3, the working portion 7 has blade-shaped portions 25 and 31 which are located, respectively, at the front end (the right hand end in FIG. 3) and at the rear end (the left hand end in FIG. 3) of the spoon-shaped portion and which form a predetermined angle (substantially a right angle, in the illustrated embodiment) with respect to the direction of the mechanical vibration at the frequency of the ultrasonic waves, and blade-shaped portions 23 and 24 which are located at lateral portions (the upper and lower portions in FIG. 3) of the spoon-shaped portion and which extend substantially parallel with respect to the direction of the mechanical vibration. Those which are brought into direct contact with the biological tissue to perform the cutting and separating work are the blade-shaped portions 23, 24 and 25

The working portion 7 of the ultrasonic vibration-transmitting tool 5 as shown in FIG. 5 is similar to that shown in FIGS. 1 and 2, and has blade-shaped portions which are similar to the blade-shaped portions 23, 24, 25 and 31 shown in FIG. 3.

The configurations and locations of these blade-shaped portions are not specifically limited, and for example, there may be provided only the blade-shaped portion 25 forming a certain angle with respect to the direction of the mechanical vibration. Alternatively, in combination therewith one or both of the parallel blade-shaped portions 23 and 24 may be provided. Further, it should be clearly understood that the blade-shaped portion 31 may be omitted. Thus, the arrangement can be selected in accordance with the location of the portion of the body to be operated on and the object of the operation.

Figure 4:
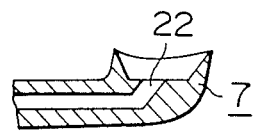
FIG. 4 is an enlarged view of a modification of a part of the working portion shown in FIG. 2.
Figure 6:
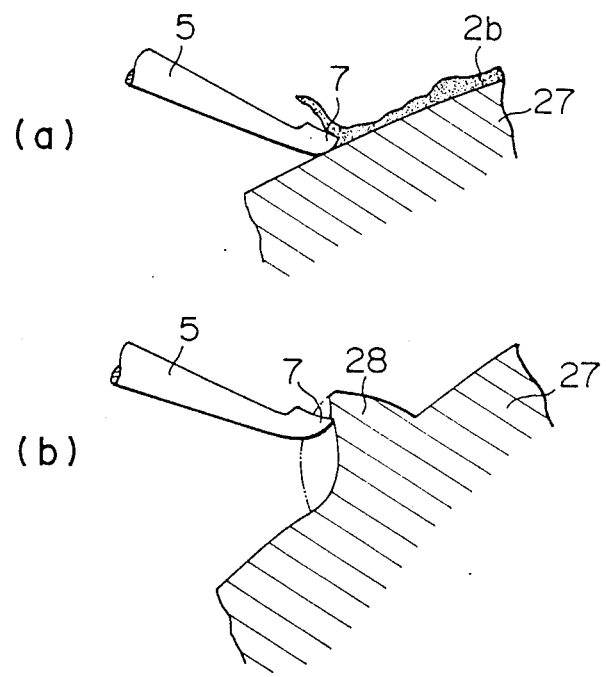
FIGS. 6 (a) and (b) are views showing examples of concrete usage of the surgical instrument in accordance with the present invention.

FIG. 6 shows examples of usage of the surgical instrument of the invention. FIG. 6 (a) illustrates an operation for separating the periosteum 2b by applying the blade-shaped portion of the spoon-shaped working portion 7 of the ultrasonic vibration-transmitting tool 5 to the boundary portion between the bone 27 and the periosteum 2b which is over the bone 27. Further, FIG. 6 (b) illustrates an operation in which the condyle 28 is cut and removed by the blade-shaped portion of the spoon-shaped working portion 7 in a decapitation. Although FIG. 6 shows the state in which the blade-shaped portion 25 located at the front end of the spoon-shaped portion is applied to the work of cutting or separating, the blade-shaped portions 23 and 24 which are located at the lateral portions of the spoon-shaped portion may be employed depending on the position and the angle of the portion of the body to be operated on, thus, making it possible to perform the operation smoothly without any great effort being required of the surgeon. The blade-shaped portions 23 and 24 may be straight as shown in FIGS. 1, 2, and 5. However, it is preferable to form them into a downwardly recessed shape as shown in FIGS. 4 and 6, since it facilitates the work of cutting and separating and allows improved efficiency of the operation to be attained.

Next, the working portion which is located at the tip end of the ultrasonic vibration-transmitting tool 5 and brought into contact with the biological tissue, and the whole part or the surface portion of which is made of a ceramic material, will be described.

When the surface portion of the ultrasonic vibration-transmitting tool 5 and the working portion 7 is made of a ceramic material, the material of the core portion is not specifically limited so long as the material is capable of transmitting the mechanical vibration at the frequency of the ultrasonic waves. However, titanium alloys which have high tensile strength and fatigue endurance are preferable. The whole part or the surface portion of the working portion 7 which is brought into direct contact with the biological tissue is formed of an inorganic material which exhibits hardness and wear resistance sufficient to prevent wear deformation of the blade-shaped portions during the work of cutting and separating hard biological tissues such as bones, and also possesses an electrical resistance property of more than $10^{13}$ $\Omega$cm which enables to prevent electric shock from being applied to the nervous tissue and the like in the event of a mere electric fault occurring in the surgical instrument. Examples of such inorganic materials are ceramic materials of the $Al_2O_3$ series, $Al_2O_3$ $-ZrO_2$ series, and $Si_3N_4$ series, though, these are not limitative. When the working portion having the surface portion formed of a ceramic material is used, the thickness of the ceramic material layer should be within the range of 1 $\mu$m to 1.5 mm, preferably, within the range of 3 $\mu$m to 1.0 mm. If the thickness is less than 1 $\mu$m, the wear resistibility will be insufficient, while if the thickness is more than 1.5 mm, the ceramic layer will easily suffer from exfoliation or breakage.

When the working portion having the surface portion made of a ceramic material is used, only the working portion 7 which is located at the tip end of the ultrasonic vibration-transmitting tool 5 may be coated with the ceramic material. Alternatively, the working portion 7 may be prepared as a separate body which is separate from the ultrasonic vibration-transmitting tool 5, and after coating the body with a ceramic material, it may be mounted and secured on the tip end of the ultrasonic vibration-transmitting tool 7 by means such as screws. When the whole of working portion is made of a ceramic material, of course a component part made of a ceramic material which constitutes the working portion 7 is mounted at the tip end of the ultrasonic vibration-transmitting tool 7 by means such as screws.

INDUSTRIAL APPLICABILITY

According to the present invention, operations involving the cutting and separating of biological tissue, particularly, cutting bones, separating the periosteum, and removing a coherent mass as a calcium mass, can be performed speedily without requiring complete mastery of the technique, as compared to the case where conventional surgical instruments are employed. Further, it is possible to maintain the activity of the biological tissue at the cut, separated surfaces by preventing frictional heat from being generated due to mechanical vibration at the frequency of the ultrasonic waves between the working portion and the biological tissue. Furthermore, it is possible to prevent reduction in the mechanical strength of the ultrasonic vibration-transmitting tool due to heat in the tool vibrated at the frequency of the ultrasonic waves. When a ceramic material is used to the spoon-shaped working portion which has blade-shaped portions, it is possible to minimize wear deformation of the blade-shaped portions. Further, it is possible to prevent any risk of causing electric shocks to be applied to the nervous tissue in the event of a simple electric fault. Thus, the instrument can preferably be used as a surgical instrument for cutting and separating biological tissue.

We claim:

1. A surgical instrument for cutting and separating biological tissue by employing ultrasonic vibration comprising:
    an ultrasonic vibration-transmitting tool adapted to perform mechanical vibration at the frequency of the ultrasonic waves;
    said ultrasonic vibration-transmitting tool including a spoon-shaped working portion adapted to be brought into contact with the biological tissue;

said spoon shaped working portion having a peripheral wall and a bottom wall and having a mortar-like recess;

said ultrasonic vibration-transmitting tool further including a liquid passage passing through the interior of said tool and having at its one side an opening which opens into a bottom portion of said working portion surrounded by said peripheral wall and which has an area smaller than an area of said bottom wall; and a blade-shaped portion provided at a top end of at least a side of said peripheral wall which forms an angle with respect to the direction of mechanical vibration at the frequency of the ultrasonic waves and a side thereof parallel with said direction of the mechanical vibration.

2. A surgical instrument as claimed in claim 1, wherein said ultrasonic vibration-transmitting tool has a connecting portion extending in a manner to form an angle with respect to the direction of mechanical vibration at the frequency of the ultrasonic waves.

3. A surgical instrument as claimed in claim 1, wherein at least a part of said working portion provided with said blade-shaped portion is made of a ceramic material.

4. A surgical instrument as claimed in claim 2, wherein at least a part of said working portion provided with said blade-shaped portion is made of a ceramic material.

5. A surgical instrument as claimed in claim 1, wherein the surface portion of at least the blade-shaped portion of said working portion is made of a ceramic material.

6. A surgical instrument as claimed in claim 2, wherein the surface portion of at least the blade-shaped portion of said working portion is made of a ceramic material.

* * * * *